(12) United States Patent
Asano et al.

(10) Patent No.: US 10,155,417 B2
(45) Date of Patent: Dec. 18, 2018

(54) PNEUMATIC TIRE

(71) Applicant: SUMITOMO RUBBER INDUSTRIES, LTD., Kobe-shi, Hyogo (JP)

(72) Inventors: Kazuo Asano, Kobe (JP); Shintaro Tomita, Kobe (JP); Susumu Tanaka, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 721 days.

(21) Appl. No.: 14/363,356

(22) PCT Filed: Jan. 18, 2013

(86) PCT No.: PCT/JP2013/050910
§ 371 (c)(1),
(2) Date: Jun. 6, 2014

(87) PCT Pub. No.: WO2013/111679
PCT Pub. Date: Aug. 1, 2013

(65) Prior Publication Data
US 2014/0332131 A1    Nov. 13, 2014

(30) Foreign Application Priority Data
Jan. 26, 2012  (JP) .................. 2012-014250

(51) Int. Cl.
*B60C 9/20*         (2006.01)
*B60C 13/00*        (2006.01)
(Continued)

(52) U.S. Cl.
CPC ............ *B60C 9/20* (2013.01); *B29D 30/0601* (2013.01); *B60C 9/0292* (2013.01); *B60C 11/03* (2013.01);
(Continued)

(58) Field of Classification Search
CPC .................. B60C 9/20; B60C 13/003
See application file for complete search history.

(56) References Cited

U.S. PATENT DOCUMENTS 4,155,392 A     5/1979  Duderstadt et al.
4,513,802 A *   4/1985  Togashi ............. B60C 3/04
                                                152/451
(Continued)

FOREIGN PATENT DOCUMENTS

EP     0 103 984 A2    3/1984
EP     0 397 380 A1   11/1990
(Continued)

OTHER PUBLICATIONS

Machine translation for Japan 11-227410 (no date).*
(Continued)

*Primary Examiner* — Steven D Maki
(74) *Attorney, Agent, or Firm* — Birch, Stewart, Kolasch & Birch, LLP (57) ABSTRACT

A pneumatic tire excellent in resistance to uneven wear, and crack resistance of a groove is provided. A position, on an equator plane, of a tread surface 20 of a tire 2 is represented as a point Pc. A position, at a maximum width, of an axially outer side surface 6a of a sidewall 6 is represented as a point Pe. A position that is a mid-point, in the radial direction, between the point Pc and the point Pe, and that is on the axially outer side surface 6a, is represented as a point Pd. When an internal pressure is enhanced from an internal pressure that is 0.05 times a normal internal pressure P to the normal internal pressure P, a value Fs of difference in amount of protrusion between an amount of protrusion Dd (mm) at the point Pd and an amount of protrusion De (mm) at the point Pe is calculated according to mathematical expression (1) in which a nominal width is represented as W (Continued)

(mm). The value Fs of difference in amount of protrusion is greater than −0.4 and less than 0.5.

$$Fs = ((Dd - De)/W) \times 100 \qquad (1)$$

2 Claims, 7 Drawing Sheets

(51) Int. Cl.
  *B60C 19/00* (2006.01)
  *B60C 9/02* (2006.01)
  *B29D 30/06* (2006.01)
  *B60C 11/03* (2006.01)
  *G01M 17/02* (2006.01)
  *G01N 3/56* (2006.01)

(52) U.S. Cl.
  CPC ............ *B60C 13/003* (2013.01); *B60C 19/00* (2013.01); *G01M 17/022* (2013.01); *G01N 3/56* (2013.01); *B29D 2030/0665* (2013.01); *B60C 2009/2012* (2013.01)

(56) References Cited

U.S. PATENT DOCUMENTS

| | | | | |
|---|---|---|---|---|
| 4,688,615 A * | 8/1987 | Lee | ...................... | B60C 9/2009 152/531 |
| 4,915,151 A | 4/1990 | Sato et al. | | |
| 4,955,416 A | 9/1990 | Takeuchi et al. | | |
| 4,976,300 A * | 12/1990 | Takehara | ................ | B60C 11/00 152/209.14 |
| 6,708,747 B1 * | 3/2004 | Tsuruta | ................ | B60C 9/2009 152/526 |
| 2001/0027836 A1 | 10/2001 | Miyazaki et al. | | |
| 2009/0229722 A1 * | 9/2009 | Isobe | ................... | B60C 9/2006 152/209.18 |

FOREIGN PATENT DOCUMENTS

| | | | |
|---|---|---|---|
| JP | 58-112804 A | | 7/1983 |
| JP | 61-200004 A | | 9/1986 |
| JP | 1-202502 A | | 8/1989 |
| JP | 02-106404 A | * | 4/1990 |
| JP | 2-106404 A | | 4/1990 |
| JP | 2-293202 A | | 12/1990 |
| JP | 4-317803 A | | 11/1992 |
| JP | 8-142602 A | | 6/1996 |
| JP | 09-202110 A | * | 8/1997 |
| JP | 11-227410 A | * | 8/1999 |
| JP | 2001-301413 A | | 10/2001 |

OTHER PUBLICATIONS

Machine translation for Japan 02-106404 (no date).*
Mark et al, Science and Technology of Rubber, 1994, pp. 678-680.*
Machine translation for Japan 09-202110 (no date).*
International Search Report issued in PCT/JP2013/050910, dated Apr. 23, 2013.
PCT/ISA/237—Issued in PCT/JP2013/050910 mailed on Apr. 23, 2013, with informal comments.

* cited by examiner

PNEUMATIC TIRE

TECHNICAL FIELD

The present invention relates to pneumatic tires.

BACKGROUND ART

Various pneumatic tires that include treads having improved wear resistance and various pneumatic tires in which tread surfaces include grooves having improved crack resistance and durability, have been suggested.

In JP2-106404, a pneumatic tire is suggested in which a radius of curvature of a tread, and an amount of protrusion of the tread in the case of the tire being inflated with air are specified to improve crack resistance and durability of grooves of the tread surface. For this tire, it is suggested that a difference between an amount of protrusion at the center of the tread and an amount of axially outward protrusion of the tread is set so as to be within a predetermined range. In this tire, change of an amount of protrusion of the tread and change of the radius of curvature of the tread are reduced when a low internal pressure state shifts to a standard internal pressure state.

In JP58-112804, a pneumatic tire is suggested in which a radius of curvature of a tread and a shape of shoulder-side wall portions are specified to improve resistance to uneven wear of the tread, and crack resistance in grooves of the tread. For this tire, it is suggested that a difference between shapes of the tread and the shoulder-side wall portions in the case of the tire being inflated with air, and shapes of the tread and the shoulder-side wall portions in a tire forming mold, is set so as to be within a predetermined range. For the tire, change between the shape of the mold for the tire and the shape of the tire inflated with air, is reduced.

CITATION LIST

Patent Literature

Patent Literature 1: JP2-106404
Patent Literature 2: JP58-12804

SUMMARY OF THE INVENTION

Problems to be Solved by the Invention

Components of a pneumatic tire are elastic members. The shapes of the components of the tire are changed while a low internal pressure state shifts to a standard internal pressure state. When the tire is inflated with air, stress is generated to change the shape of the tire to a balanced shape. The change of the shape is unavoidable in pneumatic tires. Therefore, the inventers have advanced development of a tire in which its shape is changed so as not to reduce wear resistance, and crack resistance in grooves when the tire is inflated with air.

An object of the present invention is to provide a pneumatic tire that is excellent in resistance to uneven wear, and crack resistance in grooves.

Solution to the Problems

A pneumatic tire according to the present invention includes a tread having an outer surface that forms a tread surface, and a pair of sidewalls that extend almost inward, in a radial direction, from ends, respectively, of the tread. The tread surface has grooves. A position, on an equator plane, of the tread surface is represented as a point Pc, a position, at a maximum width, of an axially outer side surface of each sidewall is represented as a point Pe, and a position that is a mid-point, in the radial direction, between the point Pc and the point Pe, and that is on the axially outer side surface of the sidewall, is represented as a point Pd. An internal pressure is enhanced from an internal pressure that is 0.05 times a normal internal pressure P to the normal internal pressure P. At this time, an amount of protrusion Dd (mm) at the point Pd and an amount of protrusion De (mm) at the point Pe are calculated. When a value Fs of difference in amount of protrusion is calculated according to mathematical expression (1) in which a nominal width is represented as W (mm), the value Fs of difference in amount of protrusion is greater than −0.4 and less than 0.5.

$$Fs = ((Dd - De)/W) \times 100 \quad (1)$$

Preferably, in the tire, when a value Fa of a sum of amounts of protrusions obtained as a sum of the amount of protrusion Dd (mm) at the point Pd and the amount of protrusion De (mm) at the point Pe is calculated according mathematical expression (2), the value Fa satisfies mathematical expression (3) and mathematical expression (4) in which an aspect ratio is A %.

$$Fa = ((Dd + De)/W) \times 100 \quad (2)$$

$$0.02626 \times A - 1.8615 < Fa \quad (3)$$

$$Fa < 0.02626 \times A - 0.66155 \quad (4)$$

Preferably, the tire includes a carcass that is extended along the tread and inner side portions of the sidewalls, and a belt layered over the carcass inward of the tread in the radial direction. The belt includes an inner layer positioned on an inner side in the radial direction, and an outer layer positioned outward of the inner layer. Each of the inner layer and the outer layer includes multiple cords aligned with each other and a topping rubber. Each cord is inclined relative to the equator plane. A direction in which the cords of the inner layer are inclined relative to the equator plane and a direction in which the cords of the outer layer are inclined relative to the equator plane are opposite to each other. An absolute value θ of an inclination angle satisfies mathematical expression (5) and mathematical expression (6) in which an aspect ratio is A %.

$$-0.1 \times A + 27.5 < \theta \quad (5)$$

$$\theta < -0.1 \times A + 31.5 \quad (6)$$

A test method according to the present invention is a test method fox a pneumatic tire including a tread having an outer surface that forms a tread surface, and a pair of sidewalls that extend almost inward, in a radial direction, from ends, respectively, of the tread.

A position, on an equator plane, of the tread surface is represented as a point PC, a position, at a maximum width, of an axially outer side surface of each sidewall is represented as a point Pe, and a position that is a mid-point, in the radial direction, between the point Pc and the point Pe, and that is on the axially outer side surface of the sidewall, is represented as a point Pd. In the test method, when an internal pressure is enhanced from an internal pressure that is 0.05 times a normal internal pressure P to the normal internal pressure P, a difference in amount of protrusion between an amount of protrusion Dd (mm) at the point Pd and an amount of protrusion De (mm) at the point Pe is measured. A wear resistance of the tread and a crack resistance and durability of a groove are evaluated based on the difference in amount of protrusion.

Preferably, in the test method, a sum of amounts of protrusions obtained as a sum of the amount of protrusion Dd (mm) at the point Pd and the amount of protrusion De (mm) at the point Pe is measured. A wear resistance of the tread and a crack resistance and durability of the groove are evaluated based on the sum of amounts of protrusions.

Preferably, in the test method, a value Fs of difference in amount of protrusion is calculated as the difference in amount of protrusion. The value Fs is calculated according to mathematical expression (1) in which a nominal width is represented as W (mm).

$$Fs=((Dd-De)/W)\times 100 \qquad (1)$$

Preferably, in the test method, an evaluation as to whether or not the value Fs is greater than −0.4 and less than 0.5 is made.

Preferably, in the test method, a value Fa of a sum of amounts of protrusions is calculated as the sum of amounts of protrusions. The value Fa is calculated according to mathematical expression (2) in which a nominal width is represented as W (mm).

$$Fa=((Dd+De)/W)\times 100 \qquad (2)$$

Preferably, in the test method, an evaluation as to whether or not the value Fa satisfies mathematical expression (3) and mathematical expression (4) in which an aspect ratio is A %, is made.

$$0.02626\times A-1.8615<Fa \qquad (3)$$

$$Fa<0.02626\times A-0.66155 \qquad (4)$$

Preferably, in the test method, the tire includes: a carcass that is extended along the tread and inner side portions of the sidewalls; and a belt layered over the carcass inward of the tread in the radial direction. The belt includes an inner layer positioned on an inner side in the radial direction, and an outer layer positioned outward of the inner layer. Each of the inner layer and the outer layer includes multiple cords aligned with each other and a topping rubber. Each cord is inclined relative to the equator plane. A direction in which the cords of the inner layer are inclined relative to the equator plane and a direction in which the cords of the outer layer are inclined relative to the equator plane are opposite to each other. A wear resistance of the tread and a crack resistance and durability of the groove are evaluated based on an absolute value θ of an inclination angle.

Preferably, in the test method, an evaluation as to whether or not the absolute value θ of the inclination angle satisfies mathematical expression (5) and mathematical expression (6) in which an aspect ratio is A %, is made.

$$-0.1\times A+27.5<\theta \qquad (5)$$

$$\theta<-0.1\times A+31.5 \qquad (6)$$

Preferably, in the test method, the absolute value θ of the inclination angle is changed to adjust the amount of protrusion Dd (mm) and the amount of protrusion De (mm).

In a tire manufacturing method for manufacturing a tire according to the present invention, the tire includes: a tread having an outer surface that forms a tread surface; a pair of sidewalls that extend almost inward, in a radial direction, from ends, respectively, of the tread; and a carcass that is extended along the tread and inner side portions of the sidewalls. The manufacturing method includes testing durability of a sample tire.

In the testing, a position, on an equator plane, of the tread surface is represented as a point Pc, a position, at a maximum width, of an axially outer side surface of each sidewall is represented as a point Pe, and a position that is a mid-point, in the radial direction, between the point Pc and the point Pe, and that is on the axially outer side surface of the sidewall, is represented as a point Pd. When an internal pressure is enhanced from an internal pressure that is 0.05 times a normal internal pressure P to the normal internal pressure P, a difference in amount of protrusion between an amount of protrusion Dd (mm) at the point Pd and an amount of protrusion De (mm) at the point Pe is measured. A wear resistance of the tread and a crack resistance and durability of a groove are evaluated based on the difference in amount of protrusion.

In the manufacturing method, the tire is designed and manufactured based on an evaluation result in the testing.

Preferably, in the manufacturing method, a carcass line is adjusted based on the evaluation result in the testing.

Preferably, in the manufacturing method, the tire includes a belt that is layered over the carcass inward of the tread in the radial direction. The belt includes a cord and a topping rubber. An absolute value θ of an inclination angle of the cord of the belt relative to the equator plane is adjusted based on the evaluation result in the testing.

Advantageous Effects of the Invention

In the pneumatic tire according to the present invention, generation of cracks in groove bottoms is reduced. In the tire, generation of uneven wear of a tread is reduced. In the test method according to the present invention, durability of a pneumatic tire can be easily evaluated. A designing method according to the present invention enables a tire excellent in durability to be easily obtained.

DESCRIPTION OF EMBODIMENTS

The following will describe in detail the present invention based on preferred embodiments with reference where appropriate to the accompanying drawing.

Figure 1:
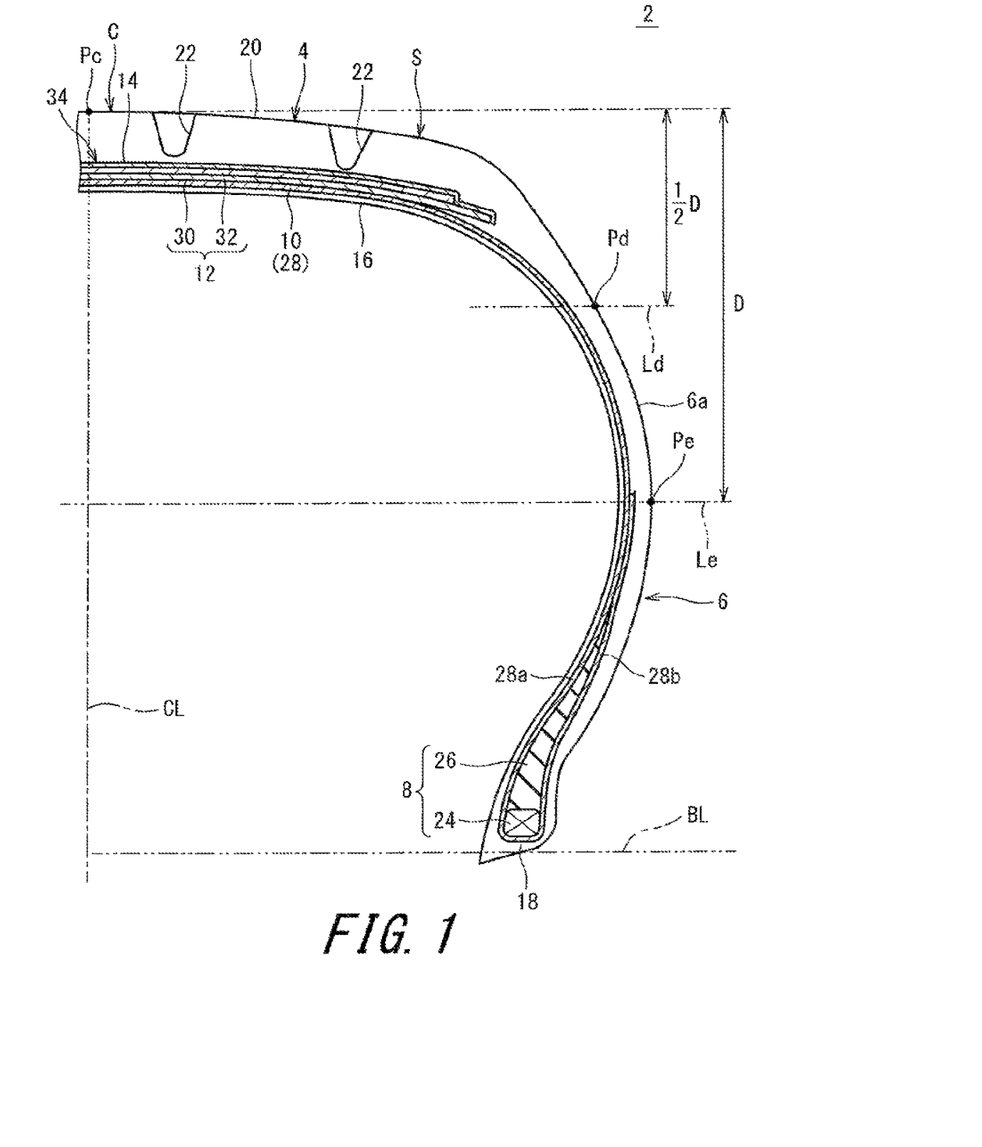
FIG. 1 is a cross-sectional view of a portion of a pneumatic tire according to one embodiment of the present invention.

FIG. 1 illustrates a pneumatic tire 2. In FIG. 1, the up-down direction represents the radial direction of the tire 2, the right-left direction represents the axial direction of the tire 2, and the direction perpendicular to the surface of the sheet represents the circumferential direction of the tire 2. The alternate long and short dash line CL in FIG. 1 represents the equator plane of the tire 2. The tire 2 has a shape which is symmetric about the equator plane except for a tread pattern. An alternate long and two short dashes line BL represents the bead base line of the tire 2.

The tire 2 includes a tread 4, sidewalls 6, beads 6, a carcass 10, a belt 12, a band 14, an inner liner 16, and chafers 18. The tire 2 is of a tubeless type. The tire 2 is mounted to passenger cars.

The tread 4 has a shape that projects outward in the radial direction. An arrow C in FIG. 1 represents a center region of the tread 4. An arrow S represents a shoulder region of the tread 4. The center region C is positioned at the center, in the axial direction, of the tire 2. A pair of the shoulder regions S is positioned outward of the center region C in the axial direction. The tread 4 forms a tread surface 20 that can contact with a road surface. The tread surface 20 has grooves 22 formed therein. A tread pattern is formed by the grooves 22.

The tread 4 includes a base layer and a cap layer, which are not shown. The cap layer is positioned outward of the base layer in the radial direction. The cap layer is layered over the base layer. The base layer is formed of a crosslinked rubber excellent in adhesiveness. A typical base rubber of the base layer is a natural rubber. The cap layer is formed of a crosslinked rubber excellent in wear resistance, heat resistance, and grip performance.

Each sidewall 6 extends from the edge of the tread 4 in almost radially inward direction. The outer ends, in the radial direction, of the sidewalls 6 are joined to the tread 4. The sidewalls 6 are formed of a crosslinked rubber excellent in cut resistance and weather resistance. The sidewalls 6 prevent the carcass 10 from being damaged.

The beads 8 are positioned inward of the sidewalls 6 in the radial direction. Each bead 8 includes a core 24 and an apex 26 that extends outward of the core 24 in the radial direction. The core 24 is ring-shaped, and includes a non-stretchable wound wire. A typical material of the wire is a steel. The apex 26 is tapered outward in the radial direction. The apex 26 is formed of a highly hard crosslinked rubber.

The carcass 10 includes a carcass ply 28. The carcass ply 28 is extended along the tread 4 and the sidewalls 6 on and between the beads 8 on both sides. The carcass ply 28 is turned up around each core 24 from the inner side toward the outer side in the axial direction. By the carcass ply 28 being turned up, the carcass ply 28 includes a main body portion 28a and turned-up portions 28b.

The carcass ply 28 is formed of multiple cords aligned with each other, and a topping rubber. An absolute value of an angle of each cord relative to the equator plane ranges from 75° to 90°. In other words, the carcass 10 forms a radial structure. The cords are formed of an organic fiber. Examples of the preferable organic fiber include polyester fibers, nylon fibers, rayon fibers, polyethylene naphthalate fibers, and aramid fibers. The carcass 10 may be formed of two or more plies.

The belt 12 is positioned inward of the tread 4 in the radial direction. The belt 12 is layered over the carcass 10. The belt 12 reinforces the carcass 10. The belt 12 includes an inner layer 30 and an outer layer 32. As is apparent from FIG. 1, the width of the inner layer 30 is slightly greater than the width of the outer layer 32 in the axial direction.

Figure 2:
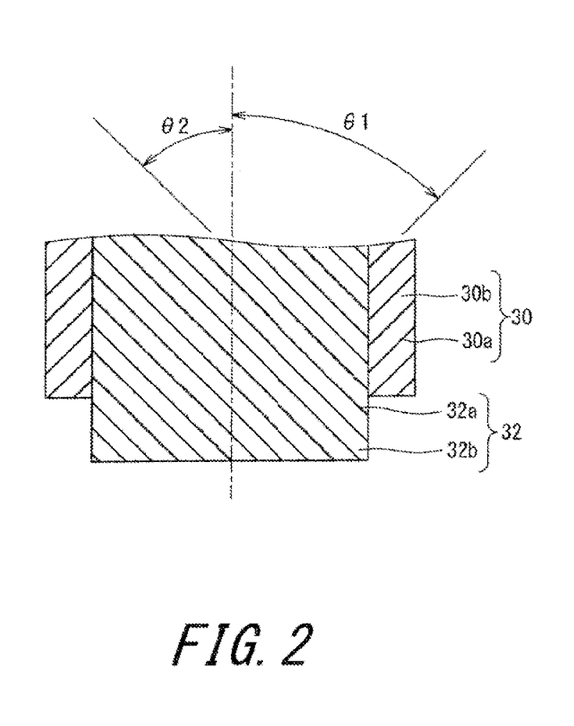
FIG. 2 illustrates a portion of a belt of the tire shown in FIG. 1.

A structure of the belt 12 will be described with reference to FIG. 2. The inner layer 30 of the belt 12 includes multiple cords 30a aligned with each other, and a topping rubber 30b. The cords 30a are inclined relative to the equator plane. A double-headed arrow $\theta1$ represents an inclination angle of each cord 30a relative to the equator plane. The outer layer 32 includes multiple cords 32a aligned with each other, and a topping rubber 32b. The cords 32a are inclined relative to the equator plane. A double-headed arrow $\theta2$ represents an inclination angle of each cord 32a relative to the equator plane.

An inclination direction in which the cords 30a of the inner layer 30 are inclined relative to the equator plane is opposite to an inclination direction in which the cords 32a of the outer layer 32 are inclined relative to the equator plane. In the tire 2, the absolute value of the inclination angle $\theta1$ and the absolute value of the inclination angle $\theta2$ are equal to each other. The absolute value of the inclination angle $\theta1$ and the absolute value of the inclination angle $\theta2$ may be different from each other. The absolute value $\theta$ for each of the inclination angle $\theta1$ and the inclination angle $\theta2$ is, for example, greater than or equal to 10°, and not greater than 35°. A material of each of the cords 30a and 32a is preferably a steel. For the cords 30a and 32a, an organic fiber may be used. A width, in the axial direction, of the belt 12 is preferably greater than or equal to 0.7 times the maximum width of the tire 2. The belt 12 may have three or more layers.

The band 14 shown in FIG. 1 is positioned outward of the belt 12 in the radial direction. The width of the band 14 is greater than the width of the belt 12 in the axial direction. The band 14 is formed of a cord and a topping rubber, which are not shown. The cord is helically wound. The band 14 has a so-called jointless structure. The cord extends substantially in the circumferential direction. An angle of the cord relative to the circumferential direction is less than or equal to 5°, and more preferably less than or equal to 2°. The cord holds the belt 12, thereby preventing lifting of the belt 12. The cord is formed of an organic fiber. Preferable examples of the organic fiber include nylon fibers, polyester fibers, rayon fibers, polyethylene naphthalate fibers, and aramid fibers.

The belt 12 and the band 14 form a reinforcing layer 34. The reinforcing layer 34 may be formed merely by the belt 12. The reinforcing layer 34 may be formed merely by the band 14.

The inner liner 16 is positioned inward of the carcass 10. The inner liner 16 is formed of a crosslinked rubber. For the inner liner 16, a rubber excellent in air-tightness is used. A typical base rubber of the inner liner 16 is a butyl rubber or halogenated butyl rubber. The inner liner 16 maintains internal pressure of the tire.

The chafers 18 are positioned near the beads 8. When the tire 2 is mounted to a rim, the chafers 18 contact with the rim. Regions near the beads 8 are protected due to the contact. For example, the chafers 18 are formed of a fabric and a rubber impregnated into the fabric.

In FIG. 1, a point Pc represents a point of intersection between the equator plane and the tread surface 20. An alternate long and two short dashes line Le represents a straight line that extends in the axial direction at the maximum width of the tire 2. The maximum width represents a width, in the axial direction, of the tire at a position where the main body portion 28a of the carcass 10 passes through the outermost portion in the axial direction. A point Pe represents a point of intersection between the straight line Le and an outer side surface 6a, in the axial direction, of each sidewall 6. The maximum width of the tire 2 is measured as a distance from the point Pe to the point Pe on the other side, which is not illustrated. A double-headed arrow D represents a distance, in the radial direction, from the point Pc to the point Pe. An alternate long and short dash line Ld represents a straight line that extends in the axial direction through the mid-point of the distance D. A point Pd represents a point of intersection between the straight line Ld and the outer side surface 6a, in the axial direction, of each sidewall 6. The point Pd represents the mid-point, in the radial direction, between the point Pc and the point Pe.

Figure 3:
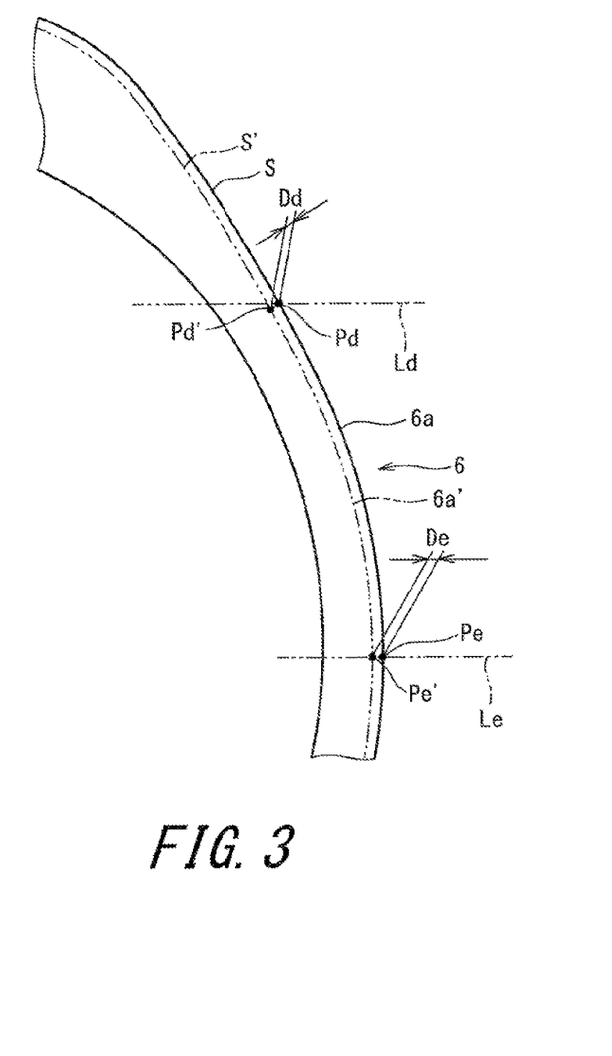
FIG. 3 is an enlarged cross-sectional view of a portion of the tire shown in FIG. 1.

FIG. 3 is an enlarged view of a portion of the tire 2. The outer side surface 6a, in the axial direction, of the tire 2 represents a state where the tire 2 is mounted to a normal rim, and is inflated with air to a normal internal pressure P. An alternate long and two short dashes line 6a' also represents the outer side surface, in the axial direction, of the tire 2. The outer side surface 6a' represents a state where the tire 2 is mounted to a normal rim, and is inflated with air to an air pressure of 0.05·P which is 0.05 times the normal internal pressure P.

A point Pd' represents a point of intersection between the outer side surface 6a' and a normal line to the outer side surface 6a in the axial direction at the point Pd. A double-headed arrow Dd represents a distance from the point Pd' to the point Pd. The distance Dd represents an amount of protrusion of the tire 2 at the point Pd. The amount of protrusion Dd represents a distance from the point Pd' to the point Pd in a state where the tire is pressurized to shift from the air pressure of 0.05·P to the air pressure P. The amount of protrusion Dd is represented so as to indicate a plus value in the case of shift in the axially outward direction and indicate a minus value in the case of shift in the axially inward direction.

A point Pe' represents a point of intersection between the straight line Le and the outer side surface 6a'. A double-headed arrow De represents a distance from the point Pe' to the point Pe. The distance De represents an amount of protrusion of the tire 2 at the point Pe. The amount of protrusion De represents a distance from the point Pe' to the point Pe in a state where the tire is pressurized to shift from the air pressure of 0.05·P to the air pressure P. The amount of protrusion De is represented so as to indicate a plus value in the case of shift in the axially outward direction, and indicate a minus value in the case of shift in the axially inward direction.

The tire 2 is mounted to a normal rim and is inflated with air to the air pressure of 0.05·P. A profile of the tire 2 under the air pressure of 0.05·P is measured by a profile measurement machine. Further, the tire is inflated with air to the air pressure P. A profile of the tire 2 under the air pressure P is measured by the profile measurement machine. The point Pe and the point Pd are obtained based on the profile of the tire 2 under the air pressure P. The profile of the tire 2 under the air pressure P and the profile of the tire 2 under the air pressure of 0.05·P are overlaid on each other such that bead positions (rim flange positions) of the profiles are aligned with each other. The straight line Le is drawn from the point Pe, and the point Pe' is obtained as a point of intersection between the straight line Le and an contour line of the profile of the tire 2 under the air pressure of 0.05·P. A normal line at the point Pd is drawn based on the contour line of the profile of the tire 2 under the air pressure P. The point Pd' is obtained as a point of intersection between the normal line and the contour line of the profile of the tire 2 under the air pressure of 0.05·P. The amount of protrusion Dd is obtained as a distance from the point Pd' to the point Pd. The amount of protrusion De is obtained as a distance from the point Pe' to the point Pe.

A value Fs of difference in amount of protrusion which represents a difference between the amount of protrusion Dd and the amount of protrusion De is calculated, based on the difference between the amount of protrusion Dd and the amount of protrusion De, and a nominal width W of the tire 2, according to mathematical expression (1) as indicated below.

$$Fs=((Dd-De)/W)\times 100 \quad (1)$$

In the tire 2, the value Fs of difference in the amount of protrusion satisfies the following mathematical expression.

$$-0.4<Fs<0.5$$

When the amount of protrusion Dd is reduced and the amount of protrusion De is increased, openings of the grooves 22 are likely to be expanded. Further, openings of the grooves 22 that extend in the circumferential direction are likely to be expanded. In particular, openings of the grooves 22 positioned in the shoulder regions S are likely to be expanded. When the openings of the grooves 22 are expanded, tensile stress is applied, in the groove width direction, to the bottom portions of the grooves 22 that extend in the circumferential direction. Due to the tensile stress, cracks are likely to be generated in the bottom portions of the grooves 22. The grooves 22 that extend in the circumferential direction include grooves that extend, in the circumferential direction, on a part of the circumference of the tread surface 20, as well as main grooves that extend, in the circumferential direction, on the entirety of the circumference of the tread surface 20.

In the tire 2, the value Fs of difference in the amount of protrusion is greater than −0.4. Therefore, the amount of protrusion Dd is prevented from being excessively less than the amount of protrusion De. In the tire 2, generation of cracks in the bottom portions of the grooves 22 is reduced.

On the other hand, when the amount of protrusion Dd is increased and the amount of protrusion De is reduced, the shoulder region S of the tread 4 is protruded in the radially outward direction. In the shoulder region S, contact pressure at the tread 4 is enhanced. When the contact pressure is high at the shoulder region S, wear of the tread surface 20 is likely to be increased.

In the tire 2, the value Fs of difference in the amount of protrusion is less than or equal to 0.5. Therefore, the amount of protrusion Dd is prevented from being excessively greater than the amount of protrusion De. In the tire 2, protrusion of the shoulder region S is reduced. In the tire 2, uneven wear of the shoulder region S is reduced.

The value Fs of difference in the amount of protrusion is represented as a ratio of a difference between the amount of protrusion Dd and the amount of protrusion De relative to the nominal width W of the tire 2. Thus, the value Fs of difference in the amount of protrusion is applicable to tires having different nominal widths W.

A value Fa of a sum, in the amount of protrusion, of the amount of protrusion Dd and the amount of protrusion De is calculated based on a sum of the amount of protrusion Dd and the amount of protrusion De, and the nominal width W of the tire 2, according to mathematical expression (2) as indicated below.

$$Fa=((Dd+De)/W)\times 100 \quad (2)$$

In the tire 2, the value Fa of the sum of the amounts of protrusions preferably satisfies the following relational expression.

$$-0.023<Fa<1.177$$

In the tire 2, an aspect ratio A is 70%. In the tire 2 having the high aspect ratio, when both the amount of protrusion Dd and the amount of protrusion De are increased, the shoulder region S of the tread 4 is likely to be protruded in the radially outward direction. By the shoulder region S being protruded, expansion of the openings of the grooves 22 is reduced. In the tire 2, the value Fa of the sum of the amounts of protrusions is greater than −0.023. Therefore, expansion of the openings of the grooves 22 is reduced. In the tire 2, generation of cracks in the groove bottoms is reduced.

On the other hand, when both the amount of protrusion Dd and the amount of protrusion De are excessively increased, protrusion of the shoulder region S of the tread 4 in the radially outward direction is increased. Contact pressure at the tread 4 is enhanced in the shoulder region S. In the shoulder region S in which the contact pressure is high, the tread surface 20 is likely to be worn. In the tire 2, the value Fa of the sum of the amounts of protrusions is less than 1.177. Therefore, protrusion of the shoulder region S is less likely to be increased. In the tire 2, uneven wear of the shoulder region S is reduced.

The value Fa of the sum of the amounts of protrusions is also represented as a ratio of the sum to the nominal width W of the tire 2. The value Fa of the sum of the amounts of protrusions is also applicable to tires having different nominal widths W.

In the tire 2, the belt 12 is formed such that two layers of the inner layer 30 and the outer layer 32 are overlaid on each other, and a direction in which the cords 30a are inclined and a direction in which cords 32a are inclined are opposite to each other. Therefore, the tread 4 can be uniformly reinforced.

In the tire 2 in which the absolute value θ of each of the inclination angle θ1 of the cords 30a and the inclination angle θ2 of the cords 32a is small, holing force by the belt 12 is high. In the tire 2 having a high holding force by the belt 12, protrusion of the tread 4 is likely to be reduced, and the amount of protrusion Dd and the amount of protrusion De are likely to be increased. In particular, in a tire, such as the tire 2, having a high aspect ratio, reduction of the absolute value θ is likely to cause increase of the amount of protrusion Dd and the amount of protrusion De.

On the other hand, in the tire 2 in which the absolute value θ is great, holding force by the belt 12 is low. In the tire 2 having a low holding force by the belt 12, protrusion of the tread 4 is likely to be increased, and the amount of protrusion Dd and the amount of protrusion De are likely to be reduced. By the absolute value θ being adjusted, adjustment of the amount of protrusion Dd and the amount of protrusion De of the tire 2 can be facilitated. Further, when the inclination angle θ1 of the cords 30a and the inclination angle θ2 of the cords 32a have the same absolute value θ, adjustment of the amount of protrusion Dd and the amount of protrusion De can be facilitated.

In the tire 2 according to the present invention, since the value Fs of difference in the amount of protrusion is greater than −0.4, and less than 0.5, generation of cracks in the bottoms of the grooves 22 and uneven wear of the tread 6 are reduced. More preferably, the sum Fa of the amounts of protrusions is within a predetermined range based on the aspect ratio, thereby enabling generation of cracks in the bottoms of the grooves 22 and uneven wear of the tread 6 to be reduced.

Figure 4:
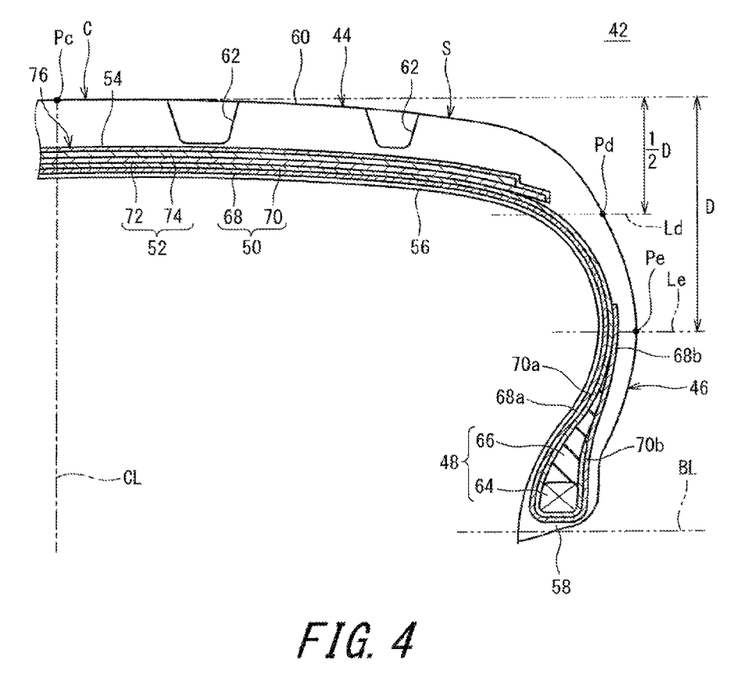
FIG. 4 is a cross-sectional view of a portion of a pneumatic tire according to another embodiment of the present invention.

FIG. 4 illustrates another pneumatic tire 42 according to the present invention. In the description herein, components thereof different from those of the tire 2 will be mainly described. Description of the same components is not given. The tire 42 includes a tread 44, sidewalls 46, beads 48, a carcass 50, a belt 52, a band 54, an inner liner 56, and chafers 58. The tire 42 is of a tubeless type. The tire 42 is mounted to passenger cars.

The tread 44 forms a tread surface 60 that can contact with a road surface. The tread surface 60 has grooves 62. Each bead 48 includes a core 64 and an apex 66 that extends outward of the core 64 in the radial direction.

The carcass 50 includes a first ply 68 and a second ply 70. The first ply 68 and the second ply 70 are extended along the tread 44 and the sidewalls 46 on and between the beads on both sides. The first ply 68 is turned up around each core 64 from the inner side toward the outer side in the axial direction. By the first ply 68 being turned up, the first ply 68 includes a main body portion 68a and turned-up portions 68b. The second ply 70 is turned up around each core 64 from the inner side toward the outer side in the axial direction. By the second ply 70 being turned up, the second ply 70 includes a main body portion 70a and turned-up portions 70b. The ends of the turned-up portions 68b of the first ply 68 are positioned radially outward of the ends of the turned-up portions 70b of the second ply 70.

Each of the first ply 68 and the second ply 70 are formed of multiple cords aligned with each other and a topping rubber. An absolute value of an angle of each cord relative to the equator plane ranges from 75° to 90°. In other words, the carcass forms a radial structure. The cords are formed of an organic fiber. Examples of the preferable organic fiber include polyester fibers, nylon fibers, rayon fibers, polyethylene naphthalate fibers, and aramid fibers. The carcass may be formed of one ply.

The belt 52 is positioned inward of the tread 44 in the radial direction. The belt 52 is layered over the carcass 50. The belt 52 includes an inner layer 72 and an outer layer 74. As is apparent from FIG. 4, the width of the inner layer 72 is slightly greater than the width of the outer layer 74 in the axial direction. Each of the inner layer 72 and the outer layer 74 is formed of multiple cords aligned with each other and a topping rubber, which are not shown. Each cord is inclined relative to the equator plane. The absolute value θ of the inclination angle is, for example, greater than or equal to 10° and not greater than 35°. A direction in which the cords of the inner layer 72 are inclined relative to the equator plane is opposite to a direction in which the cords of the outer layer 74 are inclined relative to the equator plane. A material of each cord is preferably a steel. For each cord, an organic fiber may be used. The belt 52 may have three or more layers. The belt 52 and the band 54 form a reinforcing layer 76. The reinforcing layer 76 may be formed merely by the belt 52. The reinforcing layer 76 may be formed merely by the band 54.

Also in the tire 42, the value Fs of difference in the amount of protrusion satisfies the following mathematical expression.

$$-0.4 < Fs < 0.5$$

In the tire 42, when the amount of protrusion Dd is reduced and the amount of protrusion De is increased, openings of the grooves 62 are likely to be expanded. Cracks are likely to be generated in the bottom portions of the grooves 62. In the tire 42, the value Fs of difference in the amount of protrusion is greater than −0.4. Therefore, the amount of protrusion Dd is prevented from being excessively less than the amount of protrusion De. In the tire 42, generation of cracks in the bottom portions of the grooves 62 is reduced.

On the other hand, when the amount of protrusion Dd is increased and the amount of protrusion De is reduced, the shoulder region S of the tread 44 is protruded in the radially outward direction. At the shoulder region S in which contact pressure is high, the tread surface 60 is likely to be worn. In the tire 42, the value Fs of difference in the amount of protrusion is less than or equal to 0.5. Therefore, the amount of protrusion Dd is prevented from being excessively greater than the amount of protrusion De. In the tire 42, protrusion of the shoulder region S is reduced. In the tire 42, uneven wear of the shoulder region S is reduced.

In the tire 42, the value Fs of difference in the amount of protrusion is greater than −0.4. Therefore, generation of cracks in the bottom portions of the grooves 62 is reduced. In the tire 42, the value Fs of difference in the amount of protrusion is less than or equal to 0.5. Therefore, protrusion of the shoulder region S is reduced. In the tire 42, uneven wear of the shoulder region S is reduced.

In the tire 42, the value Fa of the sum of the amounts of protrusions satisfies the following relational expression.

$$-0.811 < Fa < 0.389$$

In the tire 42, an aspect ratio is 40%. In the tire 42 having the low aspect ratio, even when both the amount of protrusion Dd and the amount of protrusion De are increased, protrusion of the shoulder region S of the tread 44 in the radially outward direction is small. An effect of reducing expansion of the openings of the grooves 62 is low. On the other hand, when both the amount of protrusion Dd and the amount of protrusion De are increased, the shoulder region S of the tread 44 is drawn in the axially outward direction. Thus, in the tire 42, openings of the grooves 67 that extend in the circumferential direction are expanded.

In the tire 42, the value Fa of the sum of the amounts of protrusions is less than 0.389. Therefore, expansion of the openings of the grooves 62 that extend in the circumferential direction is reduced. In the tire 2, generation of cracks in the groove bottoms is reduced.

In the tire 42, the span of each sidewall 46 in the radial direction is short. Since the span in the radial direction is short, when both the amount of protrusion Dd and the amount of protrusion De are reduced, protrusion of the shoulder region S of the tread 44 in the radially outward direction is likely to be increased. In the shoulder region S, contact pressure at the tread 44 is enhanced. In the shoulder region S, the tread surface 60 is likely to be worn.

In the tire 42, the value Fa of the sum of the amounts of protrusions is greater than −0.811. Therefore, protrusion of the shoulder region S is less likely to be increased. In the tire 42, uneven wear of the shoulder region S is reduced.

In the tire 42 in which the absolute value θ of the inclination angle of each cord of the belt 52 is small, holding force by the belt 52 is high. In the tire 42 having a high holding force by the belt 52, protrusion of the tread 44 is likely to be reduced, and the amount of protrusion Dd and the amount of protrusion De are likely to be increased. On the other hand, in the tire 42 in which the absolute value θ is great, holding force by the belt 52 is low. In the tire 42 having a low holding force by the belt 52, protrusion of the tread 44 is likely to be increased and the amount of protrusion Dd and the amount of protrusion De are likely to be reduced. In particular, in the tire 42 having a low aspect ratio, increase of the absolute value θ is likely to cause reduction of the amount of protrusion Dd and the amount of protrusion De. By the absolute value θ being adjusted, adjustment of the amount of protrusion Dd and the amount of protrusion De of the tire 42 can be facilitated.

A preferable range for the value Fa of the sum of the amounts of protrusions depends on an aspect ratio as described for the tire 2 and the tire 42 as examples. The inventors have produced samples of various tires having different aspect ratios. For these tires, a relationship between the value Fa of the sum of the amounts of protrusions and the value Fs of difference in the amount of protrusion, and generation of cracks in the groove bottoms and generation of uneven wear of the shoulder region S, have been examined.

Figure 5:
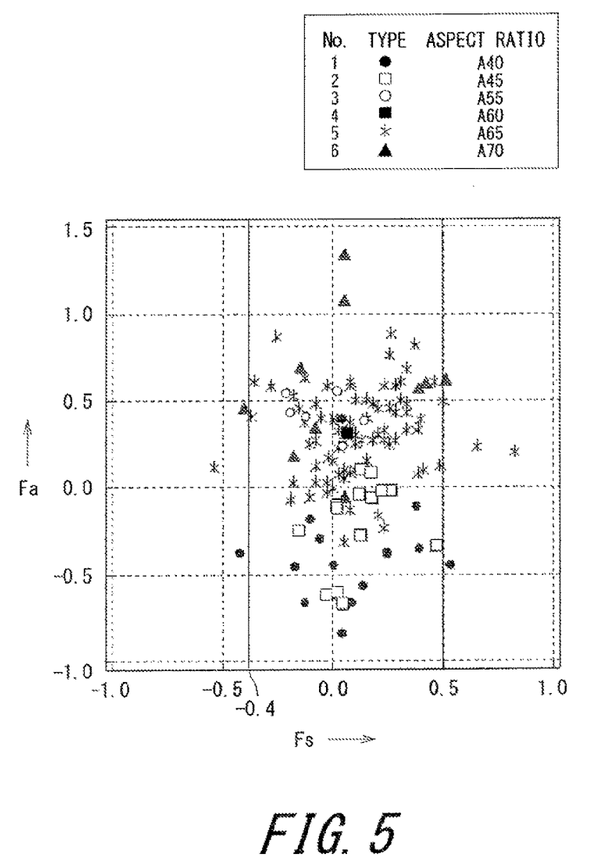
FIG. 5 shows a graph representing a relationship between a value Fs of difference in amount of protrusion and a value Fa of a sum of amounts of protrusions.

FIG. 5 shows a graph representing a distribution, of the sample tires, based on the value Fa of the sum of the amounts of protrusions and the value Fs of difference in the amount of protrusion. FIG. 5 shows a distribution of various tires having aspect ratios ranging from 40% to 70%. A40 represents a tire having an aspect ratio of 40%, and A45 represents a tire having an aspect ratio of 45%. Similarly, A55, A60, A65, and A70 represent tires having aspect ratios of 55%, 60%, 65%, and 70%, respectively. In the graph, the horizontal axis represents the value Fs of difference in the amount of protrusion, and the vertical axis represents the value Fa of the sum of the amounts of protrusions. According to the distribution of the sample tires, it has been confirmed that cracks are less likely to be generated in the groove bottom in the tires in which the value Fs is greater than −0.4. On the other hand, it has been confirmed that uneven wear is less likely to be generated in the tires in which the value Fa is less than 0.5.

As shown in FIG. 5, when the value Fs of difference in the amount of protrusion satisfies the following mathematical expression, generation of cracks in the groove bottoms can be reduced, and generation of uneven wear of the shoulder region can be reduced.

$$-0.4 < Fs < 0.5$$

Figure 6:
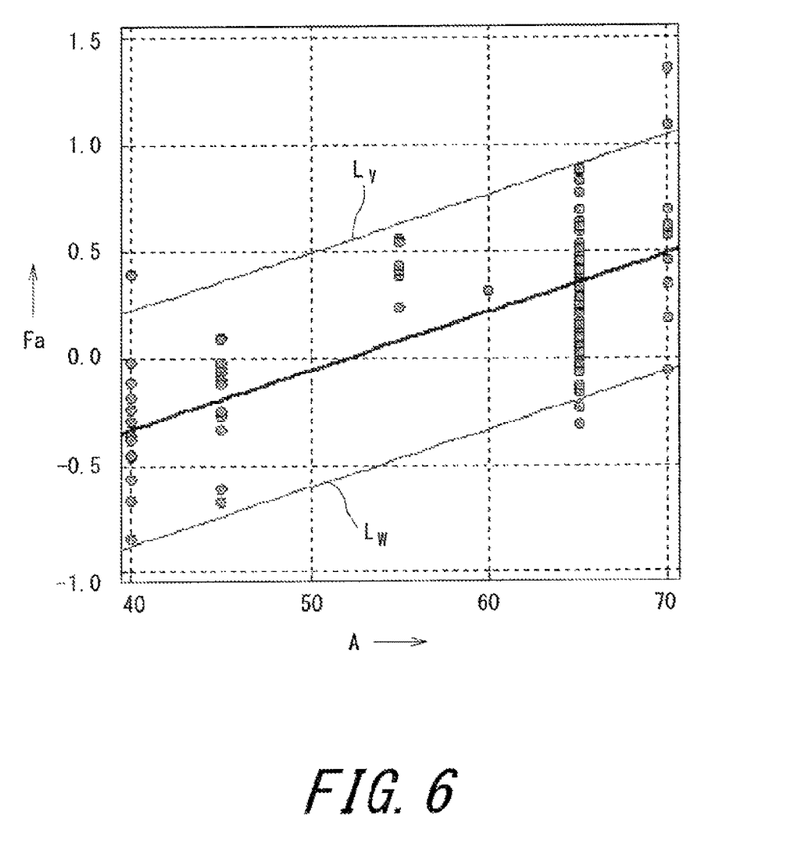
FIG. 6 shows a graph representing a relationship between an aspect ratio A and the value Fa of a sum of amounts of protrusions.

FIG. 6 shows a graph representing a distribution, of the sample tires, based on the aspect ratio A and the value Fa of the sum of the amounts of protrusions. The graph represents a distribution of the sample tires in which generation of cracks and generation of uneven wear of the shoulder region S are favorably reduced. According to the graph, it has been confirmed that, in the sample tires in which the value Fa is less than values on a straight line Lv and greater than values on a straight line Lw, generation of cracks in the groove bottoms and generation of uneven wear are particularly favorably reduced.

The straight line Lv may be represented by the following mathematical expression.

$$Fa = 0.02626 \times A - 0.6615$$

On the other hand, the straight line Lw may be represented by the following mathematical expression.

$$Fa = 0.02626 \times A - 1.8615$$

In a case where the value Fa of the sum of the amounts of protrusions satisfies mathematical expressions (3) and (4), as indicated below, in which A represents an aspect ratio, generation of cracks in the groove bottoms can be reduced and uneven wear of the tread can be reduced.

$$0.02626 \times A - 1.8615 < Fa \tag{3}$$

$$Fa < 0.02626 \times A - 0.66155 \tag{4}$$

Figure 7:
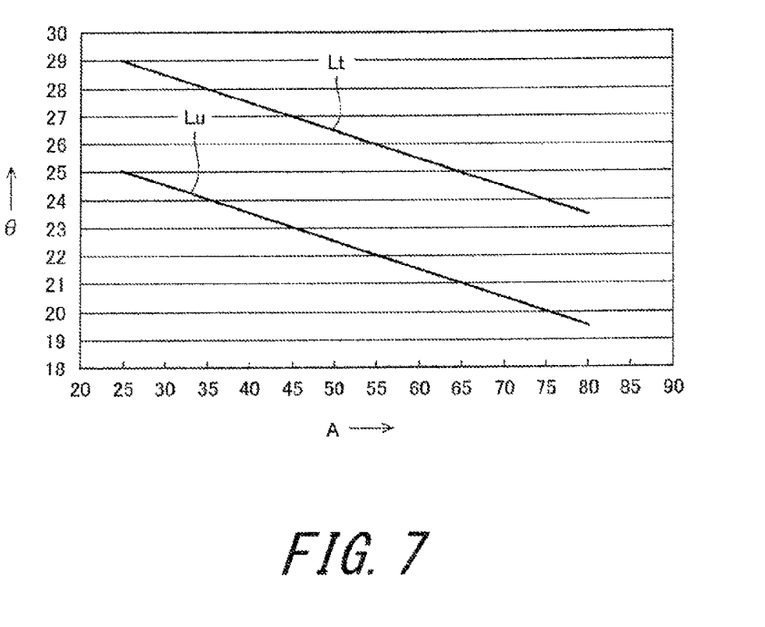
FIG. 7 shows a graph representing a relationship between the aspect ratio A and an absolute value θ of an inclination angle of cords of a belt.

FIG. 7 shows a graph obtained from a distribution, of the sample tires, based on the aspect ratio A and the absolute value θ of the inclination angle of the belt cords. A straight line Lt and a straight line Lu represent a straight line indicating upper limit values and a straight line indicating lower limit values. The straight line indicating the upper limit values and the straight line indicating the lower limit values have been confirmed from the sample tires in which generation of cracks and generation of uneven wear of the shoulder region S are favorably reduced. The straight line Lt represents upper limit values obtained from the favorable sample tires. The straight line Lu represents lower limit values obtained from the favorable sample tires.

The straight line Lt may be represented by the following mathematical expression.

$$\theta = -0.1 \times A + 31.5$$

On the other hand, the straight line Lu may be represented by the following mathematical expression.

$$\theta = -0.1 \times A + 27.5$$

When the absolute value $\theta$ of the inclination angle satisfies mathematical expressions (5) and (6) as indicated below, generation of cracks in the groove bottoms can be reduced and uneven wear of the tread can be reduced.

$$-0.1 \times A + 27.5 < \theta \tag{5}$$

$$\theta < -0.1 \times A + 31.5 \tag{6}$$

In the present invention, the dimensions and angles of the components of the tire are measured in a state where the tire is mounted to a normal rim, and the tire is inflated with air to a normal internal pressure, unless otherwise specified. During the measurement, no load is applied to the tire. In the description herein, the normal rim represents a rim that is specified according to the standard with which the tires comply. The "standard rim" in the JATMA standard, the "Design Rim" in the TRA standard, and the "Measuring Rim" in the ETRTO standard are included in the normal rim. In the description herein, the normal internal pressure represents an internal pressure that is specified according to the standard with which the tires comply. The "maximum air pressure" in the JATMA standard, the "maximum value" recited in "TIRE LOAD LIMITS AT VARIOUS COLD INFLATION PRESSURES" in the TRA standard, and the "INFLATION PRESSURE" in the ETRTO standard, are included in the normal internal pressure.

Next, a method for manufacturing the tire according to the present invention will be described. Whether or not a tire having been produced as a sample tire is good is determined based on the difference in the amount of protrusion. When it is determined that the difference in the amount of protrusion is to be rejected, for example, a shape of a mold for vulcanization molding is adjusted to adjust a carcass line such that the difference in the amount of protrusion is within a predetermined range. The carcass line is adjusted by adjusting, for example, a radius of curvature of the carcass line near the point Pd and a radius of curvature of the carcass line near the point Pe. Thus, a sample tire having an advantageous difference in the amount of protrusion is obtained. Tires are manufactured based on the sample tire.

More preferably, whether or not the sum of the amounts of protrusions is good is determined as well as whether or not the difference in the amount of protrusion is good is determined. Also when the sum of the amounts of protrusions is adjusted, for example, the carcass line is adjusted such that the sum of the amounts of protrusions is within a predetermined range. Tires are manufactured based on a sample tire having an advantageous sum of the amounts of protrusions, thereby enabling more favorable tires to be manufactured.

As a method for adjusting the difference in the amount of protrusion so as to be within the predetermined range, an exemplary method in which the carcass line is adjusted is described. However, the adjustment method is not limited to the above-described exemplary method. For example, the difference in the amount of protrusion may be adjusted by adjusting a thickness of rubber of the sidewall near the point Pd and a thickness of rubber of the sidewall near the point Pe. As a method for adjusting the sum of the amounts of protrusions so as to be within the predetermined range, a method similar to the method for adjusting the difference in the amount of protrusion so as to be within the predetermined range may be used.

Further, the absolute value $\theta$ of the inclination angle of the cords of the belt may be changed to adjust the amount of protrusion Dd and the amount of protrusion De. By the absolute value $\theta$ of the inclination angle being changed, adjustment of the amount of protrusion Dd and the amount of protrusion De can be facilitated. By the absolute value $\theta$ of the inclination angle being adjusted, manufacturing of favorable tires can be facilitated.

An exemplary test method for determining whether or not the tire is good, based on the difference in the amount of protrusion, will be described. This test method includes a step of obtaining a tire assembly, a step of measuring a low internal pressure, a step of measuring a normal internal pressure, and a determination step. In the step of obtaining a tire assembly, the tire is mounted to a normal rim, to obtain a tire assembly.

In the step of measuring a low internal pressure, the tire assembly is inflated with air to an air pressure of 0.05·P, as an internal pressure, which is 0.05 times the normal internal pressure P. In a state where the tire has been inflated with air to the air pressure of 0.05·P, a profile on which positions of the point Pd' and the point Pe' of the tire can be identified, can be obtained. In the step of measuring the normal internal pressure, after the step of measuring the low internal pressure, the tire is inflated with air to the normal internal pressure. In a state where the tire has been inflated with air to the normal internal pressure P, a profile on which positions of the point Pd and the point Pe can be identified, can be obtained.

In the determination step, based on the profile obtained when the tire is inflated with air to the normal internal pressure P, the positions of the point Pd and the point Pe are identified. Based on the profile obtained when the tire is inflated with air to the air pressure of 0.05·P, the positions of the point Pd' and the point Pe' are identified. Based on the position of the point Pd and the position of the point Pd', the amount of protrusion Dd is calculated. Based on the position of the point Pe and the position of the point Pe', the amount of protrusion De is calculated. The difference in the amount of protrusion is calculated based on a difference between the amount of protrusion Dd and the amount of protrusion Dd. Whether or not the difference in the amount of protrusion is within a predetermined range is determined. When the difference in the amount of protrusion is within the predetermined range, the tire is determined as being good. When the difference in the amount of protrusion is not within the predetermined range, it is determined that the tire is to be rejected.

In the test method, evaluation is made based on the difference between the amount of protrusion Dd and the amount of protrusion De. Therefore, determination as to durability of the tire can be efficiently performed in terms of generation of cracks in the bottom portions of the grooves and generation of uneven wear. As the difference in the amount of protrusion used for the determination step, for example, the value Fs as described above may be used. The predetermined range for the difference in the amount of protrusion may be such a range that the value Fs is greater than −0.4 and less than 0.5.

The test method preferably includes determining whether or not the tire is good based on a sum of the amounts of protrusions. In the determination step of this test method, the sum of the amounts of protrusions is calculated based on a sum of the amount of protrusion Dd and the amount of protrusion Dd. Whether or not the sum of the amounts of protrusions is within the predetermined range is determined. When the sum of the amounts of protrusions is within the predetermined range, the tire is determined as being good. When the difference in the amount of protrusion is not within the predetermined range, it is determined that the tire is to be rejected.

When evaluation is made based on the sum of the amount of protrusion Dd and the amount of protrusion De, whether or not durability is advantageous is more efficiently determined with enhanced accuracy in terms of generation of cracks in the bottom portions of the grooves, and generation of uneven wear. As the sum of the amounts of protrusions used for the determination step, for example, the value Fa as described above may be used. The predetermined range for the sum of the amounts of protrusions may be represented by mathematical expressions (3) and (4) as indicated below.

$$0.02626 \times A - 1.8615 < Fa \quad (3)$$

$$Fa < 0.02626 \times A - 0.66155 \quad (4)$$

The test method preferably includes determining whether or not the tire is good based on the absolute value θ of the inclination angle of the cords of the belt. In the determination step, whether or not the absolute value θ of the inclination angle is within a predetermined range is determined. When the absolute value θ of the inclination angle is within the predetermined range, the tire is determined as being good. When the absolute value θ of the inclination angle is not within the predetermined range, it is determined that the tire is to be rejected.

When evaluation is made based on the absolute value θ, whether or not durability is advantageous is more efficiently determined with enhanced accuracy in terms of generation of cracks in the bottom portions of the grooves and generation of uneven wear. Further, by the absolute value θ being adjusted, adjustment of the amount of protrusion Dd and the amount of protrusion De can be facilitated, thereby enabling improvement to a favorable tire to be facilitated. For the absolute value θ of the inclination angle used for the determination step, for example, mathematical expressions (5) and (6) as indicated above may be used.

$$-0.1 \times A + 27.5 < \theta \quad (5)$$

$$\theta < -0.1 \times A + 31.5 \quad (6)$$

EXAMPLES

Hereinafter, effects of the present invention will become apparent according to examples. However, the present invention should not be restrictively construed based on the description of examples.

Example 1

A tire having the fundamental structure shown in FIG. 1 was produced as a sample tire. The size of the tire was "185/70R14". Namely, the nominal width W of the tire was 185 (mm), and the aspect ratio A thereof was 70%. The tire was mounted to a normal rim of 14×5.5J. The tire was inflated with air to an internal pressure of 12 kPa. Thereafter, the tire was inflated with air to the normal internal pressure of 240 kPa. For the tire, the amount of protrusion Dd (mm), the amount of protrusion De (mm), the value Fs of difference in the amount of protrusion, and the value Fa of the sum of the amounts of protrusions, were obtained. The results are indicated in Table 1.

Example 2 to 4 and Comparative Example 1 to 2

Tires were produced as sample tires in the same manner as for example 1 except that the carcass lines were adjusted. For the tires, the amount of protrusion Dd (mm), the amount of protrusion De (mm), the value Fs of difference in the amount of protrusion, and the value Fa of the sum of the amounts of protrusions, were obtained. The results are indicated in Table 1.

Example 5

A tire having the fundamental structure shown in FIG. 4 was produced as a sample tire. The size of the tire was "225/40R18". Namely, the nominal width W of the tire was 225 (mm), and the aspect ratio A thereof was 40%. The tire was mounted to a normal rim of 18×8J. The tire was inflated with air to an internal pressure of 12 kPa. Thereafter, the tire was inflated with air to the normal internal pressure of 240 kPa. For the tire, the amount of protrusion Dd (mm), the amount of protrusion De (mm), the value Fs of difference in the amount of protrusion, and the value Fa of the sum of the amounts of protrusions, were obtained. The results are indicated in Table 2.

Example 6 to 9 and Comparative Example 3 to 4

Tires were produced as sample tires in the same manner as for example 5 except that the carcass lines were adjusted. For the tires, the amount of protrusion Dd (mm), the amount of protrusion De (mm), the value Fs of difference in the amount of protrusion, and the value Fa of the sum of the amounts of protrusions, were obtained. The results are indicated in Table 2.

Example 10

A tire having the fundamental structure shown in FIG. 1 was produced as a sample tire. The size of the tire was "185/70R14". In the tire, the cords of the inner layer of the belt and the cords of the outer layer of the belt were inclined relative to the equator plane in the directions opposite to each other. The absolute value θ of the inclination angle of each cord was 22.5°. The tire was mounted to a normal rim of 14×5.5J. The tire was inflated with air to an internal pressure of 12 kPa. Thereafter, the tire was inflated with air to the normal internal pressure of 240 kPa. For the tire, the amount of protrusion Dd (mm), the amount of protrusion De (mm), the value Fs of difference in the amount of protrusion, and the value Fa of the sum of the amounts of protrusions, were obtained. The results are indicated in Table 3.

Example 11 to 14

Tires were each produced as a sample tire in the same manner as for example 10 except that the absolute value θ of the inclination angle was changed. For the tires, the amount of protrusion Dd (mm), the amount of protrusion De (mm), the value Fs of the difference in the amount of protrusion, and the value Fa of the sum of the amounts of protrusions, are indicated in Table 3.

Example 15

A tire was produced as a sample tire in the same manner as for example 10 except that the carcass line was adjusted. For the tire, the amount of protrusion Dd (nm), the amount of protrusion De (mm), the value Fs of difference in the amount of protrusion, and the value Fa of the sum of the amounts of protrusions, were obtained. The results are indicated in Table 4.

Example 16 to 19

Tires were each produced as a sample tire in the same manner as for example 15 except that the absolute value θ of the inclination angle was changed. For the tires, the amount of protrusion Dd (mm), the amount of protrusion De (mm), the value Fs of difference in the amount of protrusion, and the value Fa of the sum of the amounts of protrusions, are indicated in Table 4.

Example 20

A tire having the fundamental structure shown in FIG. 4 was produced as a sample tire. The size of the tire was "225/40R18". In the tire, for the cords of the belt, the absolute value θ of the inclination angle was 25.5°. The tire was mounted to a normal rim of 18×8J. The tire was inflated with air to an internal pressure of 12 kPa. Thereafter, the tire was inflated with air to the normal internal pressure of 240 kPa. For the tire, the amount of protrusion Dd (mm), the amount of protrusion De (mm), the value Fs of difference in the amount of protrusion, and the value Fa of the sum of the amounts of protrusions, were obtained. The results are indicated in Table 5.

Example 21 to 24

Tires were each produced as a sample tire in the same manner as for example 20 except that the absolute value θ of the inclination angle was changed. For the tires, the amount of protrusion Dd (mm), the amount of protrusion De (mm), the value Fs of difference in the amount of protrusion, and the value Fa of the sum of the amounts of protrusions, are indicated in Table 5.

Example 25

A tire was produced as a sample tire in the same manner as for example 20 except that the carcass line was adjusted. For the tire, the amount of protrusion Dd (mm), the amount of protrusion De (mm), the value Fs of difference in the amount of protrusion, and the value Fa of the sum of the amounts of protrusions, were obtained. The results are indicated in Table 6.

Example 26 to 29

Tires were each produced as a sample tire in the same manner as for example 25 except that the absolute value θ of the inclination angle was changed. For the tires, the amount of protrusion Dd (mm), the amount of protrusion De (mm), the value Fs of difference in the amount of protrusion, and the value Fa of the sum of the amounts of protrusions, are indicated in Table 6.

Example 30

Further, a tire was produced as a sample tire in the same manner as for example 20 except that the carcass line was adjusted. For the tire, the amount of protrusion Dd (mm), the amount of protrusion De (mm), the value Fs of difference in the amount of protrusion, and the value Fa of the sum of the amounts of protrusions, were obtained. The results are indicated in Table 7.

Example 31 to 34

Tires were each produced as a sample tire in the same manner as for example 30 except that the absolute value θ of the inclination angle was changed. For the tires, the amount of protrusion Dd (mm), the amount of protrusion De (mm), the value Fs of difference in the amount of protrusion, and the value Fa of the sum of the amounts of protrusions, are indicated in Table 7.

[Evaluation for Expansion of Cut Opening]

The tires produced as the sample tires were mounted to the normal rims, to obtain the tire assemblies. Each tire assembly was inflated with air to the normal internal pressure. Bottoms of the main grooves formed in the shoulder region in the circumferential direction in each tire were cut in the circumferential direction. A razor blade having a thickness of 2.5 mm was used to cut the bottoms of the main grooves by a depth of 2 mm and a length of 8 mm. Shapes of the cut openings were taken and an amount of expansion of the cut opening was measured. The measurement results are indicated as indexes in Tables 1 to 7. The less the amount of expansion of the cut opening is, the greater the index is. The greater the index is, the less generation of crack is.

[Evaluation for Wear of Shoulder Region]

A bench measurement device for measuring wear energy was used to measure wear energy. The tires produced as the sample tires were mounted to the normal rims, to obtain tire assemblies. The tire assemblies were inflated with air to the normal internal pressure. Each tire assembly was mounted to the bench measurement device for measuring wear energy. The tire assembly was set so as to be rotatable. A slip angle was set as 1°. The tire was under a load that was 80% of the maximum load in the load index standard. The tire was settled on a setting table of the bench measurement device for measuring wear energy. Thus, wear energy of each tire in a turning state was measured.

In the measurement of wear energy, a wear energy Es in the shoulder region on the outer side in the turning radius direction and a wear energy Ec at the center region were measured. A wear energy ratio (Es/Ec) of the wear energy Es to the wear energy Ec was obtained. As the wear energy ratio (Es/Ec) is increased, the shoulder region is more likely to be worn as compared to the center region, and uneven wear is more likely to be increased. The wear energy ratio (Es/Ec) is indicated as an index and the results are indicated in Tables 1 to 7. The less the wear energy ratio (Es/Ec) is, the greater the index is. The greater the index is, the less generation of uneven wear of the shoulder region is.

[Average Score of Evaluation]

An average of the index in the evaluation for expansion of cut opening and the index in the evaluation for wear of the shoulder region was obtained. The averages are indicated as average scores of the evaluation in Tables 1 to 7. The greater the average score is, the better the result is.

TABLE 1

Evaluation results

| | Example 1 | Example 2 | Comparative example 1 | Comparative example 2 | Example 3 | Example 4 |
|---|---|---|---|---|---|---|
| Dd (mm) | 0.25 | 1.05 | 0.05 | 1.05 | 0 | 1.3 |
| De (mm) | 0.4 | 0.95 | 0.8 | 0.1 | −0.1 | 1.2 |
| Fs | −0.08 | 0.05 | −0.41 | 0.51 | 0.05 | 0.05 |
| Fa | 0.35 | 1.08 | 0.46 | 0.62 | −0.05 | 1.35 |
| Expansion of cut in groove | 8 | 8 | 6 | 8 | 7 | 9 |
| Wear at shoulder region | 9 | 8 | 8 | 6 | 9 | 7 |
| Average score of evaluation | 8.5 | 8.0 | 7.0 | 7.0 | 8.0 | 8.0 |

TABLE 2

Evaluation results

| | Example 5 | Example 6 | Example 7 | Comparative example 3 | Comparative example 4 | Example 8 | Example 9 |
|---|---|---|---|---|---|---|---|
| Dd (mm) | 0.3 | −0.15 | −0.65 | −0.9 | 0.1 | −0.9 | 0.5 |
| De (mm) | −0.55 | −0.7 | −0.85 | 0.05 | −1.1 | −1.0 | 0.4 |
| Fs | 0.38 | 0.24 | 0.09 | −0.42 | 0.53 | 0.04 | 0.04 |
| Fa | −0.11 | −0.38 | −0.67 | −0.38 | −0.44 | −0.84 | 0.40 |
| Expansion of cut in groove | 8 | 9 | 8 | 8 | 6 | 7 | 9 |
| Wear at shoulder region | 8 | 8 | 8 | 6 | 8 | 9 | 7 |
| Average score of evaluation | 8.0 | 8.5 | 8.0 | 7.0 | 7.0 | 8.0 | 8.0 |

TABLE 3

Evaluation results

| | Example 13 | Example 11 | Example 10 | Example 12 | Example 14 |
|---|---|---|---|---|---|
| Dd (mm) | 0.3 | 0.275 | 0.25 | 0.2 | 0.15 |
| De (mm) | 0.48 | 0.43 | 0.4 | 0.32 | 0.22 |
| Fs | −0.10 | −0.08 | −0.08 | −0.06 | −0.04 |
| Fa | 0.42 | 0.38 | 0.35 | 0.28 | 0.20 |
| θ (°) | 19.0 | 20.5 | 22.5 | 24.5 | 26.0 |
| Expansion of cut in groove | 9 | 9 | 9 | 9 | 8 |
| Wear at shoulder region | 8 | 9 | 9 | 9 | 9 |
| Average score of evaluation | 8.5 | 9.0 | 9.0 | 9.0 | 8.5 |

TABLE 4

Evaluation results

| | Example 18 | Example 16 | Example 15 | Example 17 | Example 19 |
|---|---|---|---|---|---|
| Dd (mm) | 1.1 | 1.075 | 1.05 | 1.0 | 0.95 |
| De (mm) | 1.03 | 0.98 | 0.95 | 0.87 | 0.77 |
| Fs | 0.04 | 0.05 | 0.05 | 0.07 | 0.10 |
| Fa | 1.15 | 1.11 | 1.08 | 1.01 | 0.93 |
| θ (°) | 19.0 | 20.5 | 22.5 | 24.5 | 26.0 |
| Expansion of cut in groove | 9 | 9 | 9 | 9 | 8 |
| Wear at shoulder region | 7 | 8 | 9 | 8 | 8 |
| Average score of evaluation | 8.0 | 8.5 | 9.0 | 8.5 | 8.0 |

TABLE 5

Evaluation results

| | Example 23 | Example 21 | Example 20 | Example 22 | Example 24 |
|---|---|---|---|---|---|
| Dd (mm) | 0.4 | 0.35 | 0.3 | 0.25 | 0.2 |
| De (mm) | −0.35 | −0.45 | −0.55 | −0.65 | −0.75 |
| Fs | 0.33 | 0.36 | 0.38 | 0.40 | 0.42 |
| Fa | 0.02 | −0.04 | −0.11 | −0.18 | −0.24 |
| θ (°) | 22.0 | 23.5 | 25.5 | 27.5 | 28.5 |
| Expansion of cut in groove | 9 | 8 | 9 | 9 | 8 |
| Wear at shoulder region | 7 | 9 | 9 | 8 | 8 |
| Average score of evaluation | 8.0 | 8.5 | 9.0 | 8.5 | 8.0 |

TABLE 6

Evaluation results

| | Example 28 | Example 26 | Example 25 | Example 27 | Example 29 |
|---|---|---|---|---|---|
| Dd (mm) | −0.05 | −0.1 | −0.15 | −0.2 | −0.25 |
| De (mm) | −0.5 | −0.6 | −0.7 | −0.8 | −0.9 |
| Fs | 0.20 | 0.22 | 0.24 | 0.27 | 0.29 |
| Fa | −0.24 | −0.31 | −0.38 | −0.44 | −0.51 |
| θ (°) | 22.0 | 23.5 | 25.5 | 27.5 | 28.5 |
| Expansion of cut in groove | 10 | 8 | 10 | 10 | 9 |
| Wear at shoulder region | 7 | 9 | 9 | 8 | 8 |
| Average score of evaluation | 8.5 | 8.5 | 9.5 | 9.0 | 8.5 |

TABLE 7

Evaluation results

| | Example 33 | Example 31 | Example 30 | Example 32 | Example 34 |
|---|---|---|---|---|---|
| Dd (mm) | −0.57 | −0.62 | −0.67 | −0.72 | −0.77 |
| De (mm) | −0.65 | −0.75 | −0.85 | −0.95 | −1.05 |
| Fs | 0.04 | 0.06 | 0.08 | 0.10 | 0.12 |
| Fa | −0.54 | −0.61 | −0.68 | −0.74 | −0.81 |
| θ (°) | 22.0 | 23.5 | 25.5 | 27.5 | 28.5 |
| Expansion of cut in groove | 9 | 8 | 9 | 9 | 8 |
| Wear at shoulder region | 7 | 9 | 9 | 8 | 8 |
| Average score of evaluation | 8.0 | 8.5 | 9.0 | 8.5 | 8.0 |

As indicated in Tables 1 to 7, scores of evaluation are higher in the tires according to examples than in the tires according to Comparative examples. The evaluation results clearly indicate that the present invention is superior. Further, as indicated in Tables 3 to 7, by the absolute value θ of the inclination angle being adjusted, adjustment of the amount of protrusion Dd and the amount of protrusion De can be facilitated. Thus, manufacturing of a pneumatic tire having an excellent resistance to uneven wear and excellent crack resistance of grooves can be facilitated.

INDUSTRIAL APPLICABILITY

The tire and the method for testing durability of the tire as described above are also applicable to various pneumatic tires for use in passenger cars, lightweight trucks, small trucks, trucks, buses, two-wheeled automotive vehicles, and to durability tests for the pneumatic tires.

DESCRIPTION OF THE REFERENCE CHARACTERS 2, 42 . . . tire
4, 44 . . . tread
6, 46 . . . sidewall
8, 48 . . . bead
10, 50 . . . carcass
12, 52 . . . belt
14, 54 . . . band
16, 56 . . . inner liner
18, 58 . . . chafer
20, 60 . . . tread surface
22, 62 . . . groove

The invention claimed is:

1. A pneumatic tire comprising a tread having an outer surface that forms a tread surface, and a pair of sidewalls that extend almost inward, in a radial direction, from ends, respectively, of the tread, wherein the tread surface has grooves,
   wherein
   a position, on an equator plane, of the tread surface is represented as a point Pc, a position, at a maximum width, of an axially outer side surface of each sidewall is represented as a point Pe, and a position that is a mid-point, in the radial direction, between the point Pc and the point Pe, and that is on the axially outer side surface of the sidewall, is represented as a point Pd, and
   when an internal pressure is enhanced from an internal pressure that is 0.05 times a normal internal pressure P to the normal internal pressure P, and a value Fs of difference in amount of protrusion between an amount of protrusion Dd (mm) at the point Pd and an amount of protrusion De (mm) at the point Pe is calculated according to mathematical expression (1) in which a nominal width is represented as W (mm),
   the value Fs of difference in amount of protrusion is less than 0.5:

$$Fs = ((Dd - De)/W) \times 100 \tag{1},$$

wherein
   when a value Fa of a sum of amounts of protrusions obtained as a sum of the amount of protrusion Dd (mm) at the point Pd and the amount of protrusion De (mm) at the point Pe is calculated according mathematical expression (2),
   the value Fa satisfies mathematical expression (3) and mathematical expression (4) in which an aspect ratio is A %:

$$Fa = ((Dd + De)/W) \times 100 \tag{2}$$

$$0.02626 \times A - 1.8615 < Fa \tag{3}$$

$$Fa < 0.02626 \times A - 0.66155 \tag{4}, \text{ and}$$

the amount of protrusion Dd is greater than the amount of protrusion De.

2. The tire according to claim 1, comprising
   a carcass that is extended along the tread and inner side portions of the sidewalls, and
   a belt layered over the carcass inward of the tread in the radial direction, the belt including an inner layer positioned on an inner side in the radial direction, and an outer layer positioned outward of the inner layer, wherein
   each of the inner layer and the outer layer includes multiple cords aligned with each other and a topping rubber,
   each cord is inclined relative to the equator plane,
   a direction in which the cords of the inner layer are inclined relative to the equator plane and a direction in which the cords of the outer layer are inclined relative to the equator plane are opposite to each other, and
   an absolute value θ of an inclination angle of each cord satisfies mathematical expression (5) and mathematical expression (6) in which an aspect ratio is A %:

$$-0.1 \times A + 27.5 < \theta \tag{5}$$

$$\theta < -0.1 \times A + 31.5 \tag{6}.$$

* * * * *